(12) United States Patent
Hochgraeber et al.

(10) Patent No.: US 9,091,693 B2
(45) Date of Patent: Jul. 28, 2015

(54) PLUG UNIT AND CONNECTION SYSTEM FOR CONNECTING CAPILLARY TUBES, ESPECIALLY FOR HIGH-PERFORMANCE LIQUID CHROMATOGRAPHY

(75) Inventors: Hermann Hochgraeber, Offenberg-Neuhausen (DE); Adolf Satzinger, Olching (DE); Daniel Bürger, Raisting (DE); Andreas Unger, Garching (DE)

(73) Assignee: DIONEX SOFTRON GMBH, Germering (DE)

( * ) Notice: Subject to any disclaimer, the term of this patent is extended or adjusted under 35 U.S.C. 154(b) by 8 days.

(21) Appl. No.: 13/321,156

(22) PCT Filed: Mar. 19, 2010

(86) PCT No.: PCT/DE2010/000333
§ 371 (c)(1),
(2), (4) Date: Nov. 17, 2011

(87) PCT Pub. No.: WO2010/133192
PCT Pub. Date: Nov. 25, 2010

(65) Prior Publication Data
US 2012/0061955 A1    Mar. 15, 2012

(30) Foreign Application Priority Data
May 22, 2009   (DE) .......................... 10 2009 022 368

(51) Int. Cl.
*F16L 17/00*    (2006.01)
*G01N 30/60*    (2006.01)

(52) U.S. Cl.
CPC ................................. *G01N 30/6026* (2013.01)

(58) Field of Classification Search
USPC .................. 285/357, 353, 322, 323, 324, 342
See application file for complete search history.

(56) References Cited

U.S. PATENT DOCUMENTS

| 3,880,452 A | 4/1975 | Fields |
| 4,083,702 A | 4/1978 | Hartigan et al. |

(Continued)

FOREIGN PATENT DOCUMENTS

| CN | 2087340 U | 10/1991 |
| CN | 1477391 A | 2/2004 |

(Continued)

OTHER PUBLICATIONS

PCT, International Search Report for PCT Application No. PCT/DE2010/000333 dated Jul. 19, 2010 (3 pages).

(Continued)

*Primary Examiner* — Aaron Dunwoody
(74) *Attorney, Agent, or Firm* — Timothy J. Ohara

(57) ABSTRACT

A plug unit for connecting capillary tubes includes a plug housing that has an axial borehole, a plug capillary tube that projects through the axial borehole, and a sealing element that surrounds the plug capillary tube. The front end of the plug capillary tube is sealed by an elastic and/or plastic deformation of the sealing element against the capillary tube receptacle opening of a bushing unit. A hollow cylindrical pressure piece is provided that surrounds the sealing element in an axial region facing away from the end surface of the plug capillary tube, and the pressure piece has a rearward end side that faces away from the end surface of the plug capillary tube and that can be loaded by the plug housing with an axial pressure force when the plug unit and bushing unit are connected.

19 Claims, 8 Drawing Sheets

(56) References Cited

U.S. PATENT DOCUMENTS

| | | | |
|---|---|---|---|
| 4,602,809 A * | 7/1986 | Ross et al. | 285/50 |
| 4,619,473 A | 10/1986 | Someya | |
| 4,690,437 A | 9/1987 | Anderson, Jr. | |
| 4,792,396 A * | 12/1988 | Gundelfinger | 210/198.2 |
| 4,991,883 A | 2/1991 | Worden | |
| 5,601,785 A | 2/1997 | Higdon | |
| 6,273,478 B1 | 8/2001 | Benett et al. | |
| 6,494,500 B1 | 12/2002 | Todosiev et al. | |
| 6,926,313 B1 | 8/2005 | Renzi | |
| 2006/0213823 A1 | 9/2006 | Rigoli | |

FOREIGN PATENT DOCUMENTS

| | | |
|---|---|---|
| WO | 9815824 A1 | 4/1998 |
| WO | WO 99/32821 A1 | 7/1999 |
| WO | WO 01/16517 A1 | 3/2001 |

OTHER PUBLICATIONS

SIPO, Office Action issued on Sep. 11, 2013 in corresponding Chinese Patent Application No. 201080022396.X (19 pages).

SIPO, Search Report issued on Sep. 3, 2013 in corresponding Chinese Patent Application No. 201080022396.X (4 pages).

\* cited by examiner

PLUG UNIT AND CONNECTION SYSTEM FOR CONNECTING CAPILLARY TUBES, ESPECIALLY FOR HIGH-PERFORMANCE LIQUID CHROMATOGRAPHY

TECHNICAL FIELD OF THE INVENTION

The invention relates to a plug unit for connecting capillary tubes, especially for high-performance liquid chromatography. In addition, the invention relates to a connection system including a bushing unit and plug unit.

BACKGROUND OF THE INVENTION

In chromatography systems, liquids or gases are fed through suitable connection lines between the components of the relevant system. These connection lines, that can be made, for example, from stainless steel, have available at their ends suitable connection systems, also called fittings, in order to be able to create a tight connection with the connections of the components.

Such a connection system was already described in 1975 in U.S. Pat. No. 3,880,452. A capillary tube forming the connection line between two components is here pushed into the capillary tube receptacle opening of a bushing unit or connection unit and fixed in the bushing by means of an attachment screw that has a central borehole for guiding the capillary tube. For sealing, one or more sealing elements that surround the capillary tube in their front end region are pressed into the capillary tube receptacle opening that runs conically inward by means of the attachment screw when the capillary tube and bushing unit are connected.

Here, however, it is disadvantageous that the sealing position is not realized in the plane of the end surface perpendicular to the longitudinal axis of the capillary tube, but is instead offset rearward a certain distance from the end surface in the axial direction. In this way, a dead volume is produced that has a disadvantageous effect, especially in high-performance liquid chromatography. In the case of the extremely high pressures used in high-performance liquid chromatography, in order to be able to guarantee the tightness of such connections, sealing elements are often used like those described, for example, in U.S. Pat. No. 4,619,473 as state of the art (FIG. 2). That publication involves annular sealing elements that are, for the most part, likewise made from stainless steel and that have, in the longitudinal section, a conical profile of the outer diameter. Such a sealing element interacts with a conical receptacle opening in the bushing unit, wherein the conical receptacle opening has a larger angle than the sealing element relative to the longitudinal axis of the capillary tube. Here, when the sealing element is pressed into the receptacle opening, an extremely high, radially inward pressure is exerted by means of an attachment screw onto the front region of the sealing element, so that the sealing position is realized here. Through this pressure, however, for the most part, a deformation of the sealing element and the capillary tube is generated, wherein the sealing element is pressed with its front edge in an annular shape into the outer periphery of the capillary tube. Such a deformation is undesired, especially because the sealing element here is connected to the capillary tube with a positive-fit and non-positive-fit connection, and the sealing element can no longer be easily shifted in the axial direction onto the capillary tube. If the sealing connection is released and should such a plug element be screwed into another bushing unit, for example, because a component of the chromatography system must be replaced, then, indeed, a tight connection can be produced, but, due to tolerances or manufacture-dependent differences in the depth of the receptacle opening, it can no longer be guaranteed that the capillary tube applies a force again with its end surface on the end surface of the line to be connected. If the receptacle opening of the bushing unit of the exchanged component is longer in the axial direction than the previously used component, then an undesired dead volume is created. If the receptacle opening for the capillary tube in the exchanged component is shorter in the axial direction than the previously used component, then the capillary tube is even deformed, possibly damaged, by the pressure of the attachment screw, and a tight connection is no longer possible in certain circumstances. This is because the sealing element mounted on the capillary tube with a positive-fit and non-positive-fit connection cannot move in the axial direction.

However, in the case of such a fitting, a small dead volume also can be rarely avoided, if the end surfaces of the capillary tube and the line to be connected are directly opposite each other or contact each other, because the sealing position is not located in the region of the end surface of the capillary tube or the line to be connected.

In order to be able to compensate for such tolerances or in order to be able to use connection systems of different manufacturers with one and the same plug unit, a self-adjusting plug for high-performance liquid chromatography is described in U.S. Pat. No. 6,494,500 in which the capillary tube is biased axially in the direction toward the capillary tube receptacle openings of the bushing unit by means of a spring provided in the attachment screw. For the seal, an exchangeable ferrule is used that, however, has a conical construction again in its front region and interacts, for forming the seal, with an inner wall of the ferrule receptacle opening that has a more pronounced conical construction. Here, there is the risk again that the ferrule is "crimped tight" onto the capillary tube, especially when the sealing element is made from a metal, for example, stainless steel.

In addition, in this plug unit it is disadvantageous that a support element for the screw spring must be mounted on the capillary tube, wherein this support element makes the production of such a plug unit more complicated.

For avoiding a dead volume, a unit is known from U.S. Pat. No. 4,083,702 for connecting capillary tubes for gas chromatography in which the capillary tubes are similarly connected to each other with their end surfaces abutting. The capillary tubes are fixed by means of annular elements that are wedge-shaped in the longitudinal section and that interact with corresponding conical recesses in the connection housing. In this case, however, the seal is simpler relative to a connection that is compatible with high-performance liquid chromatography, because, in the case of gas chromatography, the pressures that are used are significantly lower, for example, by up to 6 bar. There is no flexibility with respect to the use of the unit for different depths of the capillary tube receptacle borehole.

In addition to the already mentioned disadvantages, the known connection systems feature the disadvantage that the risk arises that the sealing element remains in place in the relevant receptacle opening of the bushing unit when the plug unit is dismounted and the capillary tube is pulled out from the bushing unit.

In addition, the trend in high-performance liquid chromatography is toward using thinner capillary tubes, because these can be more easily bent to better adapt them to the current installation conditions. Due to the production process, thinner capillary tubes also feature smaller tolerances in the inner diameter and smaller eccentricity of the inner diameter. For using capillary tubes with smaller outer diameters in connection with conventional bushing units or connection units, these are provided at the ends with a sleeve for adapting the outer diameter to the diameter of the thicker conventional capillary tubes. However, this represents an additional expense and increases the dead volume of a connection. In addition, in the case of an unfavorable tolerance position, an additional dead volume between the sleeve and capillary tube could also be created.

The present invention is directed to a plug unit for connecting capillary tubes, especially for high-performance liquid chromatography, which can be used in a simple way for capillary tubes with different outer diameters in connection with bushing units with conventional diameters of receptacle openings and here simultaneously offers the possibility of compensating different axial tolerances of receptacle openings in bushing units. In addition, when the plug unit is dismounted, it should be avoided that the sealing element detaches from the capillary tube and remains in the bushing unit. The present invention is also directed to a connection system with such a plug unit.

SUMMARY OF THE INVENTION

Embodiments of the present invention allow capillary tubes with different outer diameters to be connected in a simple way to existing, typical bushing units in a pressure-tight way and with small or negligible dead volume. Various forms of the present invention employ a sealing element that surrounds the plug capillary tube on the front end region of the plug capillary tube. This sealing element is constructed or positioned so that the front end surface of the sealing element is flush at least with the front end surface of the plug capillary tube or projects past this surface by a relatively small axial length. The sealing element is surrounded, in a rear region, by a pressure piece and is rigidly connected with respect to axial movements relative to the plug capillary tube by means of the pressure piece. With this construction, an application of an axial force on the pressure element generated by the plug housing when the plug unit is connected to the bushing unit produces a sealing effect in the front-most region of the end surface of the plug capillary tube or the sealing element. In particular, the axial pressure force is transmitted via the pressure piece onto the sealing element and the plug capillary tube. Here, first, the plug capillary tube is fixed in the receptacle opening of the bushing unit due to the rigid attachment of the pressure piece and the sealing element on the plug capillary tube, and second, a pressure-tight seal with little or no dead volume is created in the region of the end surface of the plug capillary tube or the sealing element by the compression of the sealing element. Through the compression of the sealing element in its front-most region, a sealing effect is produced not only on the end side of the sealing element or on the end side of the plug capillary tube, but also in the radial direction with respect to the inner walls of the capillary tube receptacle opening into its innermost region. In addition, a seal is realized in the radial direction between the outer wall of the front end of the plug capillary tube and the inner wall of the sealing element, so that no additional dead volume can be produced between these elements.

Differently than in the known plug units for high-performance liquid chromatography, the sealing does not take place in the region of a conical peripheral wall of an annular element that surrounds the plug capillary tube, wherein the conical outer wall of the annular element is pressed against a complementary conical inner wall in the receptacle opening of the bushing unit.

Therefore, the plug unit according to the present invention can be adapted for use with already-existing conventional bushing units that have, as a rule, a cylindrical capillary tube receptacle opening in the innermost region, wherein this opening transitions, via a conically expanding region, into an adjacent threaded region into which the plug housing of the plug unit can be screwed. While the seal is realized in a prior art plug unit by means of a conical ferrule of the plug unit in the conically expanding region of the bushing unit, plug units according to the present invention achieve the seal with no dead volume in the innermost region of the capillary tube receptacle opening.

For adaptation, only the outer diameter of the plug unit must be adapted to the relevant inner diameter in the region in which the plug unit engages in the typically cylindrical receptacle opening of the bushing unit. This can be realized through the selection of the outer diameter for the sealing element or the outer diameter for the pressure piece. Because the sealing effect takes place in the front-most region of the plug unit, it is also possible to dismount a plug unit with such a construction and to remount it with uniform tightness with the same or also a different bushing unit whose capillary tube receptacle opening has the same inner diameter. This is because the structure of the plug unit according to the invention allows the compensation of axial tolerances, because the sealing effect takes place directly in the front-most end region of the plug capillary tube or the sealing element and a fixed distance between an axial sealing position and the front-most end of the plug unit does not have to be maintained. In this way, deformations in the region of the end surface of the plug capillary tube and weakening of the axial sealing force can be avoided when the axial length of the receptacle opening is smaller in the bushing unit than the distance between the axial sealing position and the end surface of the plug capillary tube. In the same way, a dead volume can be avoided that results when no sealing effect is given in the region of the end surface of the plug capillary tube and the axial length of the capillary tube receptacle opening of the bushing unit is greater than the axial distance between the sealing position and the end surface of the plug capillary tube.

According to one preferred embodiment of the invention, the sealing element and the pressure piece are constructed so that the outer diameter of the front region of the sealing element in which the sealing element is not surrounded by the pressure piece essentially corresponds to the outer diameter of the adjacent (rearward) region of the pressure piece. Here, via the end surface of the pressure piece that is incorporated in the material of the sealing element (for this purpose, a shoulder whose height corresponds to the wall thickness of the cylindrical pressure piece can be provided in the outer periphery of the sealing element), the axial pressure force is exerted toward the front end of the plug unit, i.e., onto the end surface of the plug capillary tube and the end surface of the sealing element (if these end surfaces are aligned flush) or onto the end surface of the sealing element (if this surface projects past the end surface of the plug capillary tube). Due to this axial pressure force transmitted to the end surface(s), the sealing element is compressed (or in connection with a compression of the plug capillary tube in its front-most region, if the plug capillary tube is made from an elastically and/or plastically deformable material), whereby not only a sealing effect is generated in the region of the end surface(s), but also because of the radial expansion of the sealing element due to the compression also in the radial direction, the outer periphery of the sealing element interacts with the inner wall of the capillary tube receptacle opening of the bushing unit (this applies at least for a certain front region of the sealing element that expands radially due to the compression).

The prerequisite here is obviously that the inner diameter of the sealing element adjacent to the plug capillary tube essentially corresponds to the outer diameter of the plug capillary tube and, in addition, the inner diameter of the capillary tube receptacle opening (in the relevant axial region) corresponds to the outer diameter of the sealing element at least in the region of the end of the connected plug capillary tube.

According to one embodiment of the invention, the sealing element can be constructed elastically so that it surrounds the plug capillary tube with biasing tension when mounted on the front region of the plug capillary tube. Here, the rigid connection between the sealing element and the plug capillary tube can be generated or supported (against relative movements in the axial direction). Such biasing tension, however, obviously can also be generated by means of the base part of the pressure piece, if the sealing element cannot apply the required biasing tension.

According to one embodiment of the invention, the pressure piece can have a two-part structure, wherein an essentially hollow cylindrical base part surrounds the plug capillary tube and, at least in one sub-region, the sealing element. This base part is composed of an annular attachment part that is crimped onto the base part so that a fixed connection is produced between the pressure piece, sealing element, and plug capillary tube by a friction fit or a positive fit generated by the deformation or a combination of these fits. For this purpose, the pressure piece can have an essentially triangular section in a longitudinal section, whose acute-angled section is curved (crimped) radially inward. According to the arrangement and structure of the sealing element and pressure piece, the radially inward directed deformation can generate a friction fit or positive fit either directly in interaction with the wall of the plug capillary tube or via a sub-region of the sealing element. In the case that the radial deformation of the pressure piece generates, via a radial deformation of the sealing element, a friction fit or friction fit and positive fit with the wall of the plug capillary tube, a more rigid connection is produced between the sealing element and the plug capillary tube, so that when detaching the connection between the plug unit and the bushing unit, the sealing element can be pulled together with the plug capillary tube and the remaining parts of the plug unit from the capillary tube receptacle opening, wherein, in this case, even high axial tensile forces that are exerted on the sealing element do not detach the connection between the sealing element and the plug capillary tube. Thus, the risk does not arise that the sealing element remains in the capillary tube receptacle opening of the bushing unit.

At this point it should be noted that, in the scope of the present description, crimping is understood to be any subsequent, radial, plastic change in shape of the pressure piece or a predetermined region of the pressure piece that is performed after the individual parts of the plug unit are assembled, especially after pushing the sealing element or the pressure piece onto the plug capillary tube.

According to one configuration of the invention, the sealing element can be connected exclusively or additionally for attachment by means of crimping through a positive fit with the pressure piece. Here, the pressure piece can have, especially at its inner periphery, a peripheral projection or individual projections that engage in a corresponding peripheral recess or in corresponding individual recesses that are provided in the corresponding outer wall of the sealing element. With reference to axial extraction forces that are exerted by the plug capillary tube or the pressure piece on the sealing element, in this way a nondetachable positive fit or a snap-in connection can be generated that permits detachment of the sealing element from the other plug unit only for extremely high extraction forces.

According to another configuration of the invention, the plug capillary tube can have a second outer jacket layer or a jacket element at least in one axial sub-region that is surrounded by the pressure piece, or, in any case, in a sub-region in which a crimped connection is produced or is to be produced. This jacket layer can either be mounted rigidly onto the plug capillary tube, for example, through extrusion coating or by the pushing on or adhering of a sleeve made from a corresponding suitable material, or through galvanic application or deposition of metals. In this way, the outer diameter of the pressure piece can be easily adapted to the inner diameter of the capillary tube receptacle opening of the bushing unit, even if the wall of the pressure piece is to have a structure thin enough to permit subsequent crimping.

In addition, by selecting a sufficiently elastic material, it can be achieved that, in the case of plug capillary tubes that are made from a hard, nondeformable, and/or brittle material, radial forces that are high enough to cause destruction or damage are not exerted on the plug capillary tube at the position at which the pressure piece is crimped.

BRIEF DESCRIPTION OF THE DRAWINGS

These and other advantages and features of the invention will be apparent from the following description of illustrative embodiments, considered along with the accompanying drawings.

The invention will be explained in greater detail below with reference to embodiments shown in the drawing. Shown in the drawing are.

DESCRIPTION OF ILLUSTRATIVE EMBODIMENTS

Figure 1:
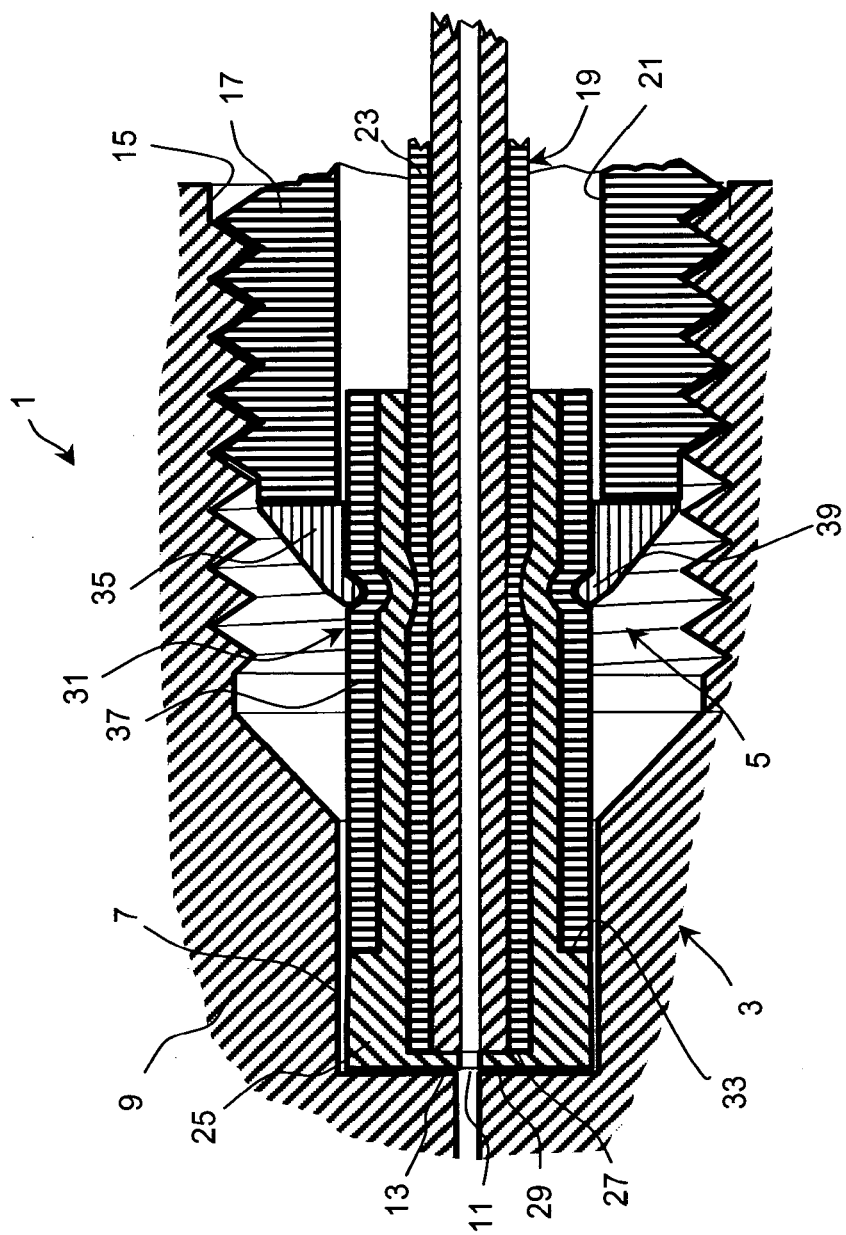
FIG. 1, a first embodiment of a connection system for connecting capillary tubes according to the invention in a longitudinal section with a capillary tube surrounded by a jacket layer in the plug region, FIG. 2, a second embodiment of a connection system similar to FIG. 1, but without a jacket layer, FIG. 3, a third embodiment of a connection system without a jacket layer, wherein the plug housing loads both the pressure piece and the sealing element in the axial direction, FIG. 4, a fourth embodiment similar to FIG. 1, wherein, however, the end surface of the plug capillary tube contacts the floor-side contact face of the capillary tube receptacle opening, FIG. 5, a fifth embodiment of a connection system according to the invention, wherein the sealing element is connected with a positive fit in a rearward region only with a front sub-region of the pressure piece, FIG. 6, a sixth embodiment similar to FIG. 5, wherein, however, the plug capillary tube has a jacket layer, FIG. 7, a seventh embodiment of a connection system according to the invention, with a conical profile of the end surface of the pressure piece and complementary shape of the sealing element, and FIG. 8, an embodiment similar to FIG. 6, wherein the jacket layer is provided in only one region within the pressure piece between the rearward end of the sealing element and the crimped position.

The connection system 1 shown in FIG. 1 in a longitudinal section for connecting capillary tubes, especially for high-performance liquid chromatography, comprises a bushing unit 3 and a plug unit 5. The bushing unit 3 is shown with only the part that is important for understanding the present invention, namely with the bushing housing 9 having the capillary tube receptacle opening 7. The bushing housing 9 can be mounted, for example, in a component of a chromatography device, for example, a chromatography column. The bushing housing 9 has a bushing capillary tube opening 11 that is constructed centrally in the floor wall 13 of the capillary tube receptacle opening 7. The capillary tube receptacle opening 7 expands into a receptacle opening 15 for a plug housing 17 of the plug unit 5. The receptacle opening 15 is here provided on its inner wall with a thread, for example, a fine thread that interacts with a corresponding thread or fine thread on the outer wall of the plug housing 17. Through the use of a fine thread, when the plug housing 17 is screwed into the receptacle opening 15, high axial pressure forces that are transmitted from the plug housing onto the other components of the plug unit 5 are generated even with low rotational moments. Thus it is possible, even for the use of the connection system 1 in high-performance liquid chromatography, to enable tool-free assembly of the plug unit 5 and the bushing unit 3 through the simple, manual screwing of the plug unit 5 into the bushing unit 3 and, nevertheless, in this way, to guarantee a pressure-tight connection.

In addition to the plug housing 17, the plug unit 5 comprises the plug capillary tube 19 that is guided through an axial borehole 21 of the plug housing 17. The outer diameter of the plug capillary tube 19 is significantly smaller than the inner diameter of the pot-shaped capillary tube receptacle opening 7. The plug capillary tube 19 can be made from a material that is suitable for guiding the relevant medium, in particular, liquid medium, for example, made from a plastic, such as PEEK, metal, for example, stainless steel, or glass. In the embodiment of the connection system shown in FIG. 1, the plug capillary tube 19 is made from a brittle material, for example, glass, so that the brittleness of this material must be taken into consideration for the assembly of the other components. For this reason, the plug capillary tube 19 has, at least in the axial area in which the plug unit 5 is provided, a jacket layer 23 that is made from a soft material, for example, PEEK, which can deform sufficiently, in particular, elastically and/or plastically. In the case of the embodiment of the connection system 1 shown in FIG. 1, the jacket layer 23 is provided across the entire axial region of the front end of the plug capillary tube 19 that is used for realizing the plug unit 5.

As can be seen from FIG. 1, the entire front end of the plug capillary tube 19 is surrounded by a sealing element 25 that has a hollow cylindrical construction before assembly on the plug capillary tube 19. The sealing element 25 shown in FIG. 1 projects past the end surface 27 of the plug capillary tube 19 and surrounds it, wherein, in the end wall 29 of the sealing element 25 that surrounds the end surface 27 of the plug capillary tube 19, an opening is obviously constructed whose inner diameter is at least as large as the inner diameter of the plug capillary tube 19 or the diameter of the bushing capillary tube opening 11 also in the mounted state of the bushing unit 3 and plug unit 5.

In the case of the embodiment according to FIG. 1, the end wall 29 of the sealing element 25 guarantees that the end surface 27 of the plug capillary tube 19 that is made from a brittle material that cannot deform or that can deform slightly plastically or elastically is not pressed indirectly by the axial pressure force against the floor wall 13 of the capillary tube receptacle opening 7 and possibly destroyed or damaged in this way (through possible high local point loading).

The sealing element 25 is surrounded in a rear region by an essentially hollow cylindrical pressure piece 31, wherein, in the entire region of the axial surrounding, the inner diameter of the pressure piece 31 essentially corresponds to the outer diameter of the sealing element 25. On the front end surface of the pressure piece 31, the sealing element 25 has a shoulder, wherein, in the front region facing the floor wall 13 of the capillary tube receptacle opening 7, the sealing element has an outer diameter that corresponds to the outer diameter of the pressure piece 31.

As can be seen from FIG. 1, the outer diameter of the pressure piece 31 can be selected slightly smaller than the inner diameter of the capillary tube receptacle opening 7, in order to enable a simple insertion of the plug unit 5. Starting from the shoulder 33, which contacts the end surface of the pressure piece 31, the sealing element can have a diameter increasing slightly in the direction toward the end surface of the sealing element, wherein the maximum diameter in the region of the end surface corresponds essentially to the inner diameter of the capillary tube receptacle opening 7.

As can be seen from FIG. 1, in the rear region of the pressure piece 31, an annular attachment part 35 is provided that surrounds the hollow cylindrical base part 37. In the axial longitudinal section, the attachment part 35 has an essentially triangular cross section, wherein the acute-angled region 39 contacting the outer surface of the base part 37 is crimped radially inward. In this way, not only is the attachment part 35 mounted on the base part 37, but the base part 37 is connected together with the sealing element 25 rigidly to the plug capillary tube 19 through the radially inward-directed deformation in the crimped region that also continues into a radial deformation of the sealing element 25 and the jacket layer 23. In the case of a practically inelastic or plastic deformable inner wall of the plug capillary tube 19, the attachment of the sealing element 25 and the pressure piece 31 is produced essentially by a friction fit. This applies at least when the jacket layer 23 is not connected rigidly to the inner wall of the plug capillary tube 19, for example, because the jacket layer 23 was pushed in the form of a separate jacket layer onto the inner wall of the plug capillary tube 19.

Obviously, however, the jacket layer 23 could also be connected rigidly to the inner wall of the plug capillary tube 19, for example, extruded onto or adhered to this part. In this case, the connection between the jacket layer 23 already connected to the other plug capillary tube 19 with the sealing element 25 and the pressure piece 31 is produced by a positive fit or a combination positive fit and friction fit, because radial deformation of the jacket layer 23 is also produced in the crimped region.

In each case, through the simple crimped connection, a connection that is resistant to axial forces is produced for the pressure piece 31 (consisting of the base part 37 and attachment part 35) and the sealing element 25 with the plug capillary tube 19. Obviously, one or more crimped positions could be provided.

The attachment part 35 of the pressure piece 31 is loaded in the axial direction on its rear end surface by the front end surface of the plug housing 17, when the plug housing 17 is screwed into the receptacle opening 15 of the bushing housing 9. These axial pressure forces are transmitted via the pressure piece 31 to the sealing element 25 and the plug capillary tube 19, wherein the sealing element 25 is pressed with its end wall 29 against the floor wall 13 of the capillary tube receptacle opening 7. Here, a pressure-tight connection is produced in the direct vicinity of the bushing capillary tube opening 11.

The pressure-tight connection is produced, however, not only by pressing the end wall 29 of the sealing element 25 against the floor wall 13 of the capillary tube receptacle opening 7, but by the compression of the sealing element 25 in its front region that results in a radial expansion of the sealing element in its front region, so that the peripheral wall of the sealing element 25 is also pressed against the cylindrical inner wall of the capillary tube receptacle opening 7.

In this way, a pressure-tight and practically dead-volume-free connection is produced, so that this connection system is also suitable for extremely low flow rates of the medium to be transported, wherein the medium can simultaneously be put under a high pressure without producing leakage in the connection. Dead-volume-free connections optimize, above all, the separating power of a chromatography system.

The axial position of the attachment part 35 on the base part 37 of the pressure piece 31 is selected so that a large axial distance is produced between the rear end of the capillary tube receptacle opening 7 or the inner end region of the receptacle 15 and the plug housing 17, so that the plug unit 5 can be used for bushing units 3 with different axial lengths of the capillary tube receptacle opening 7. A prerequisite here is that, in each case, the axial front region of the plug unit comprising the plug capillary tube 19, sealing element 25, and pressure piece 31 (or base part 37 thereof) in which an essentially constant outer diameter is given (less than the inner diameter of the capillary tube receptacle opening 7) is greater than the axial length or depth of the capillary tube receptacle opening 7. If this requirement is not fulfilled, then no or insufficient axial pressure force can be exerted on the end surface of the sealing element 25 in order to guarantee a sealing effect. Furthermore, through the selection of the dimensions of the plug unit, especially the pressure piece, it must be guaranteed that the conical region of the attachment part 35 does not collide with the conical section of the bushing housing 9 before the sealing element 25 can generate its sealing effect completely.

Obviously, instead of a screw connection between the plug housing 17 and bushing housing 9, any other suitable connection could also be used, such as, for example, a bayonet catch or a snap-in connection.

Likewise, a conical shape of the attachment part 35 of the pressure piece 31 is not absolutely required. Any other shape is conceivable that allows a crimped connection, wherein the crimped connection need not be absolutely uniform across the entire periphery. Instead, for example, simple flattening of an annular element into an essentially elliptical element is also conceivable.

The production of a plug unit according to FIG. 1 can be realized, for example, in that initially a jacket layer 23 or a corresponding jacket element is applied to the inner wall of the plug capillary tube 19. Here, both a rigid and also an initially loose connection can be provided. Then the sealing element 25 can be pushed together with the initially hollow cylindrical base part 37 of the pressure piece 31 onto the front end of the plug capillary tube 19 (including jacket layer 23). The attachment part 35 can likewise be pushed simultaneously or also subsequently onto the components named above. The plug housing 17 can be pushed either from the other end of the plug capillary tube 19 or from the same side as the other components, but at least before pushing on attachment part 35. Then these components could be inserted into an assembly bushing and the plug housing could be screwed into the assembly bushing, wherein the assembly bushing is essentially shaped as the bushing housing shown in FIG. 1. The capillary tube receptacle opening of the assembly bushing, however, has an axial length or depth that is selected so that it corresponds to the desired axial length of the plug unit from its end surface up to the crimped position. The assembly bushing here has a conical expansion that is adjacent to the capillary tube receptacle opening and whose angle of inclination is selected greater than the angle of inclination of the conical surface of the attachment part 35. In the case of such a construction of the assembly bushing by means of the plug housing 17 or a corresponding pressing tool, if a sufficiently high axial force is exerted once on the attachment part 35, then the acute-angled region 39 is crimped inward, by means of which the desired crimped connection is produced.

Figure 2:
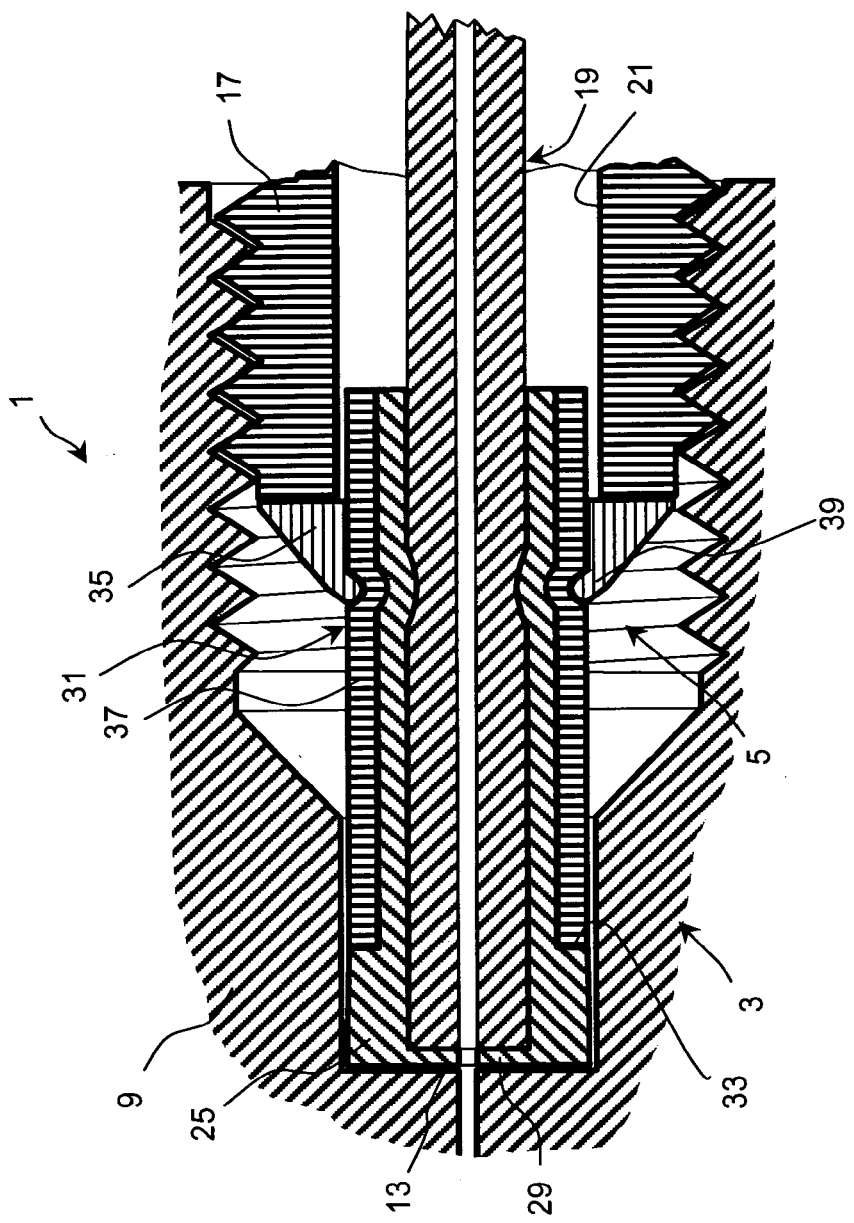

The additional embodiment of a connection system 1 shown in FIG. 2 largely corresponds to the embodiment shown in FIG. 1 and explained above in detail, wherein, however, the presence of a jacket layer 23 could be eliminated, because the plug capillary tube 19 is already made, overall, from a material that does not react so sensitively with respect to radial mechanical pressure forces. Such a plug capillary tube 19 can be made, for example, from plastic or metal or combinations of these materials (PEEK-sil=glass+jacket layer). As shown in FIG. 2, a slight plastic, radial deformation of the wall of the plug capillary tube 19 also takes place in the crimped region due to the crimped connection. The attachment is thus also realized by a combination of friction fit and positive fit between the plug capillary tube 19, the sealing element 25, and the base part 37 of the pressure piece 31.

Obviously, however, it is also conceivable that the material of the plug capillary tube 19 is so hard that no radial deformation of the outer wall of the plug capillary tube is produced in the crimped region. In this case, the connection between the plug capillary tube 19 and the sealing element 25 is realized almost exclusively by a friction fit.

Figure 3:
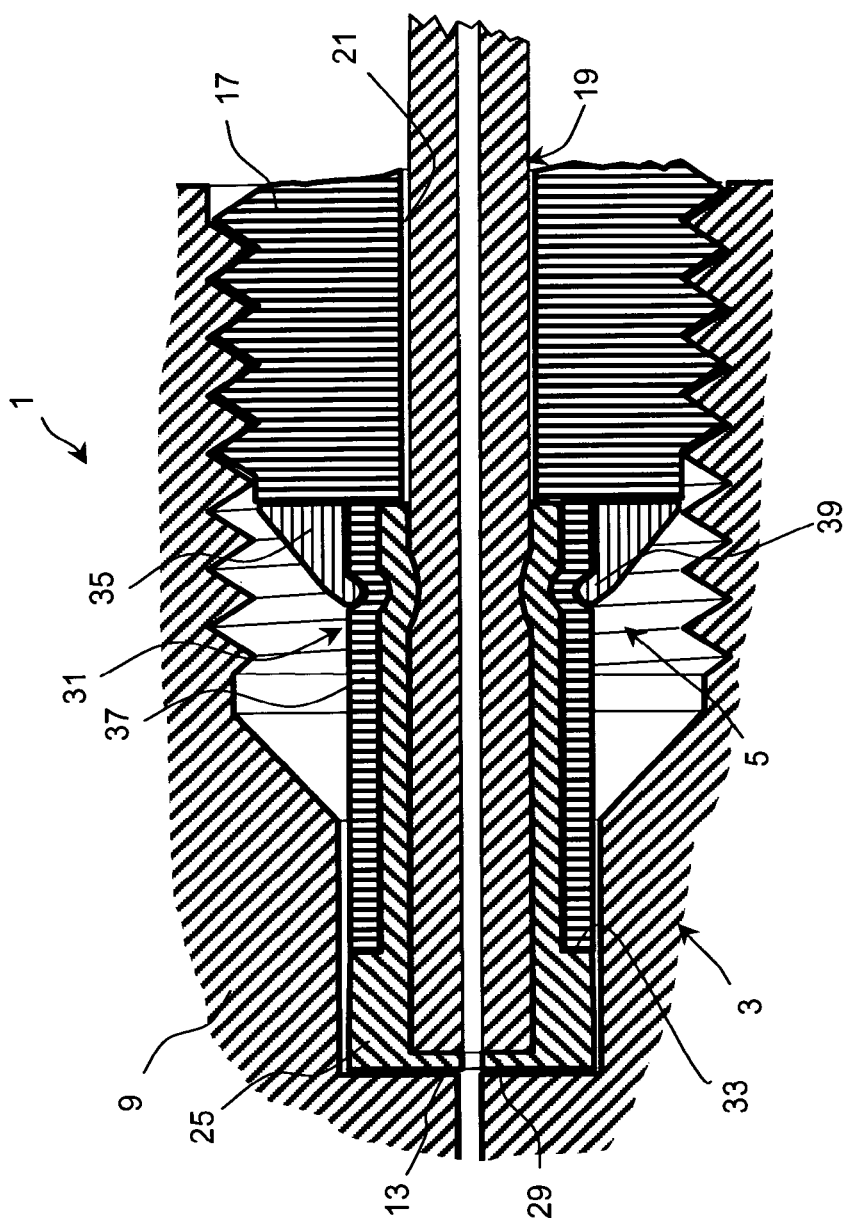

The embodiment shown in FIG. 3 corresponds, in large part, to the embodiment according to FIG. 1, wherein, however, the rear end surface of the attachment part 35 runs flush with the rear end surfaces of the base part 37 and the sealing element 25. Here it is possible to select the inner diameter of the axial borehole 21 in the plug housing 17 so that the front end surface of the plug housing 17 loads the rearward-directed end surfaces of both the attachment part 35 and also the base part 37 and the sealing element 25.

Figure 4:
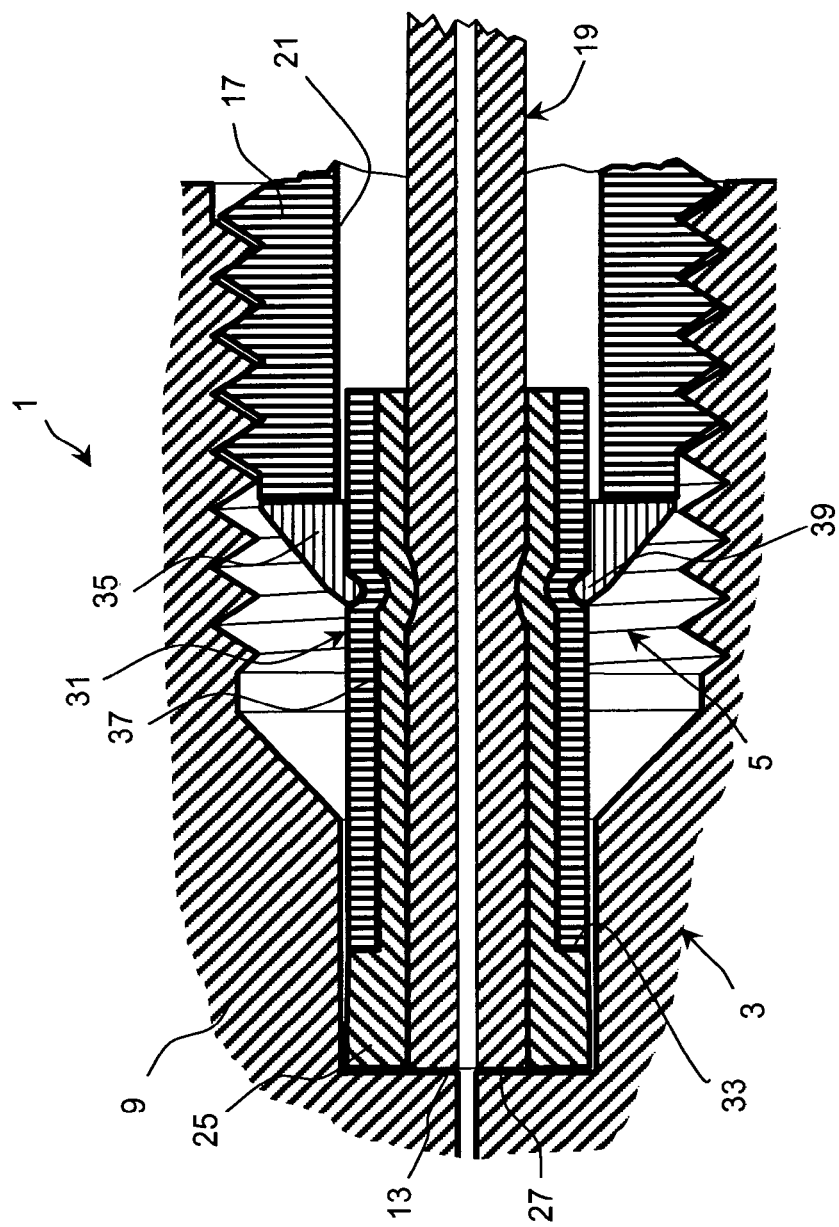

The embodiment shown in FIG. 4 of a connection system 1 is identical, up to the construction of the front region of the sealing element 25, with the embodiment according to FIG. 2. The sealing element 25 of the embodiment of a connection system 1 according to FIG. 4 no longer surrounds the end surface 27 of the plug capillary tube 19. Instead, the end surface of the sealing element 25 is formed flush with the end surface 27 of the plug capillary tube 19. In the unassembled state of the plug unit 5 and bushing unit 3, the end surface of the sealing element 25 can also project in the axial direction slightly past the end surface 27 of the plug capillary tube 19.

In the case of the assembly of a plug unit 5 constructed in this way with the bushing unit 3, for flush end surfaces of the plug capillary tube 19 and sealing element 25, both end surfaces are simultaneously pressed against the floor wall 13 of the capillary tube receptacle opening 7, when a corresponding axial pressure is exerted by means of the plug housing 17. In the case of flush end surfaces, however, the material of the plug capillary tube 19 should be at least slightly plastically or elastically deformable, so that the sealing effect is produced both in the axial direction and also in the radial direction. If the end surface of the sealing element 25 does not project slightly past the end surface of the plug capillary tube 19 in the unmounted state, then the end surface of the sealing element is first brought into contact with the floor wall 13, and the sealing element is compressed by the axial forces, so that the desired sealing effect is realized both in the region of the end surface and also in the radial direction (in the front region of the sealing element). However, the projection of the end surface of the sealing element 25 should also be selected here so that, in the final mounted state, the end surface of the plug capillary tube contacts the floor wall 13 of the capillary tube receptacle opening 7, in order to avoid undesired dead volume.

Figure 5:
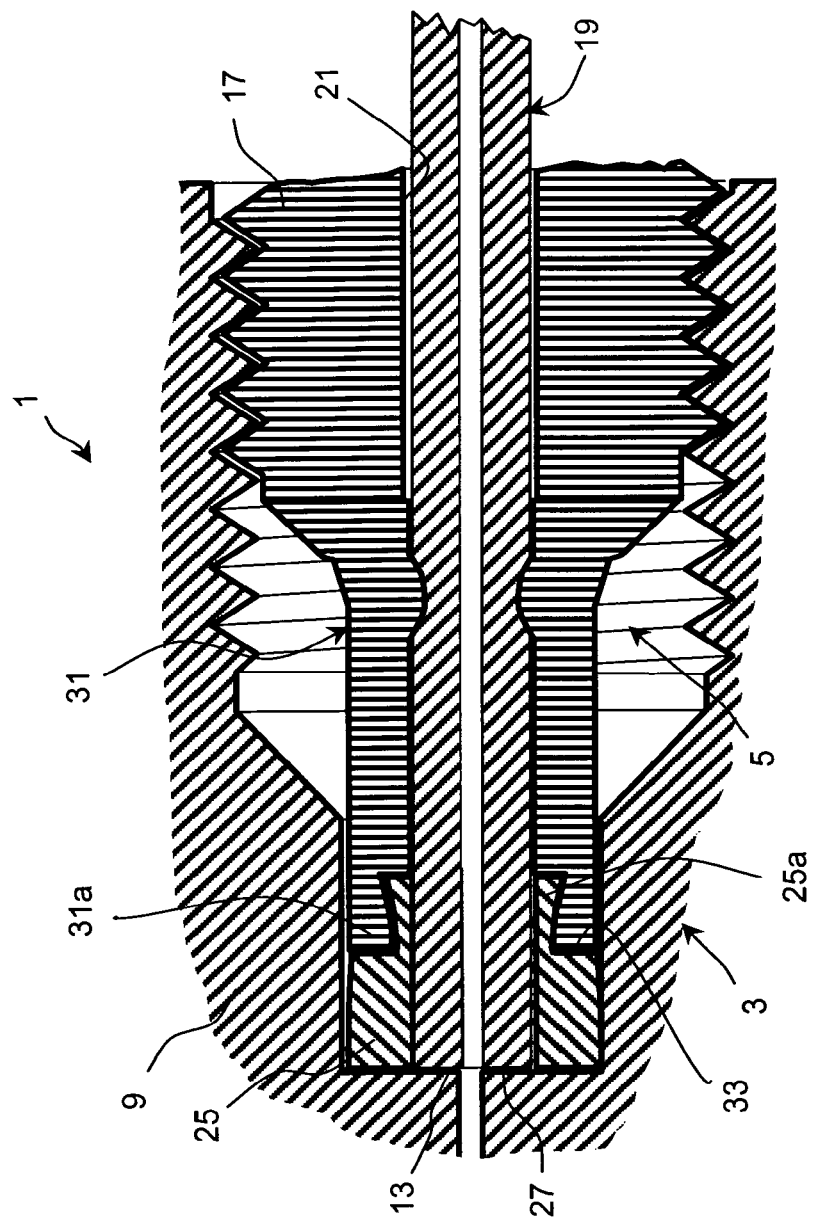

In the embodiment of a connection system 1 shown in FIG. 5, the pressure piece 31 has a one-piece structure. The sealing element 25 is constructed in turn, so that its end surface is flush with the end surface of the plug capillary tube 19 or projects slightly past this surface in the dismounted state. In a rearward attachment region 25*a*, the sealing element 25 is connected with a positive fit to an attachment region 31*a* of the pressure piece 31. The attachment region 31*a* here surrounds the attachment region 25*a*, wherein a peripheral dovetail-like attachment is produced. In this embodiment, the sealing element 25 thus does not project past the total axial length in an annular space between the pressure piece 31 and the outer wall of the plug capillary tube 19. The one-part pressure piece 31 is connected, in turn, by means of a crimped attachment in an axial, rearward region to the plug capillary tube with a positive fit and friction fit. In this embodiment, the entire rear annular end surface of the pressure piece 31 is loaded by the front end surface of the plug housing 17. Obviously, the positive fit between the sealing element 25 and the pressure piece 31 could also be produced through a subsequent, radial deformation of the pressure piece 31, that is, through crimping.

In this embodiment, the pressure piece 31 is directly connected to the plug capillary tube 19, so that axial pressure forces can be better transmitted toward the end surface of the plug capillary tube 19 and sealing element 25 than in the case in which the friction fit and/or positive fit must have been transmitted from the pressure piece 31 via a (usually softer) sealing material of the sealing element 25 to the plug capillary tube 19.

Axial tensile forces that are exerted on the sealing element when the plug unit 5 is pulled out from the bushing unit 3 are received, in the embodiment according to FIG. 5, exclusively by means of the positive fit and friction fit between the attachment region 31*a* of the pressure piece 31 and the attachment region 25*a* of the sealing element 25 and possibly the friction fit between the sealing element 25 and the plug capillary tube 19.

In contrast, in the case of embodiments according to FIGS. 1 to 4, a tensile force acting on the sealing element 25 is also received by means of the friction fit and positive fit that is produced by the crimped connection when the plug unit 5 and bushing unit 3 are disassembled.

The embodiment of a connection system 1 according to FIG. 6 is again suitable for a plug capillary tube 19 that has a jacket layer 23 that is provided at least in the axial region of the pressure piece 31 (apart from its attachment region 31*a*). The material of the inner wall of the plug capillary tube can again be glass, for example. Through the presence of the jacket layer 23 that can obviously also be formed as a separate jacket element, it is avoided, in turn, that the radial deformation also continues to the inner wall of the plug capillary tube 19. Thus, between the pressure piece 31 and the jacket layer 23 there is a positive fit and friction fit, while the connection between the jacket layer 23 and the inner wall of the plug capillary tube 19 is realized either by only a friction fit or is produced by some other type of connection, such as adhesion or the like.

In this case, the sealing element 25 also has an end wall 29 that surrounds the end surface of the plug capillary tube 19 or the end surface of the inner wall of the plug capillary tube 19, since no jacket layer 23 is provided in the front axial region in which the sealing element 25 surrounds the inner wall of the plug capillary tube 19. The end wall should avoid essentially the bursting of the end surface of brittle plug capillary tubes 19 due to local, impermissibly high point-wise loads.

Figure 6:
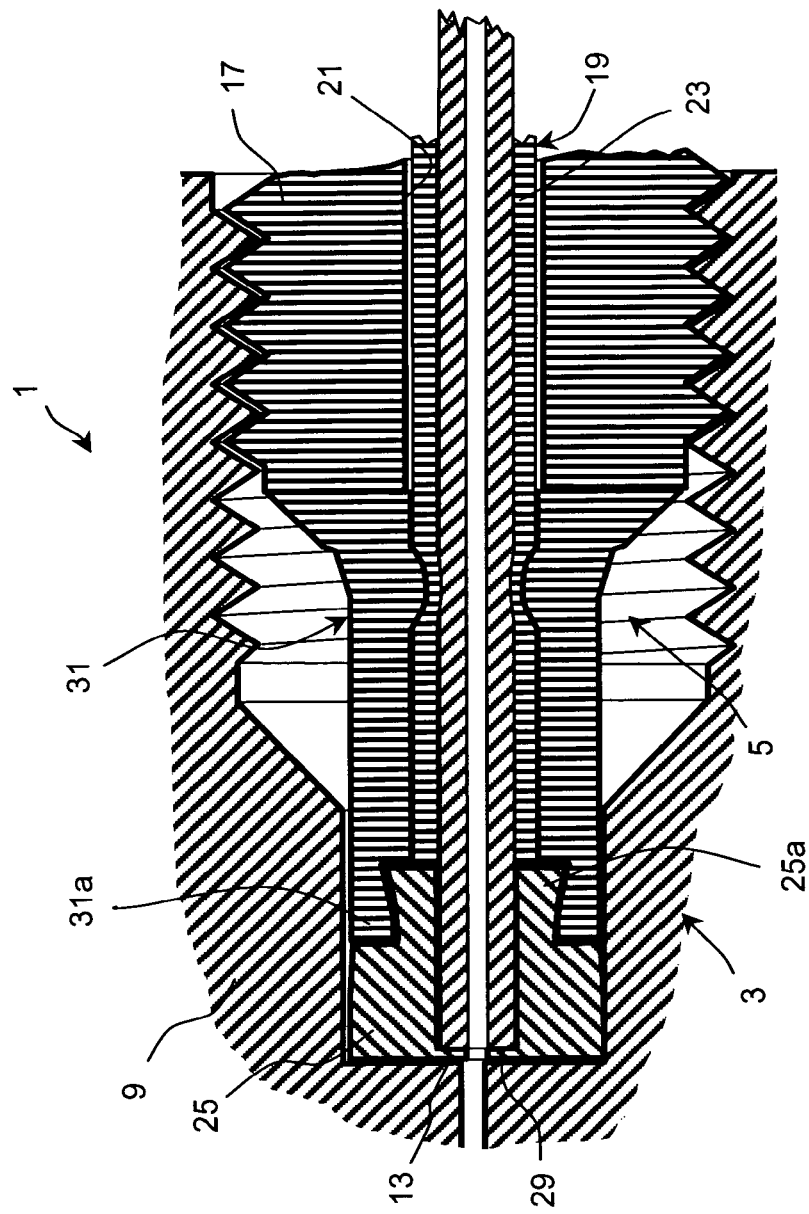

In the embodiment according to FIG. 6, also in the axial region in which the plug housing 17 surrounds the plug capillary tube 19, a jacket layer 23 is provided in order to prevent damage to the inner wall of the plug capillary tube 19.

For explanation of the functioning of the embodiment according to FIG. 6, with respect to the sealing effect, refer to the preceding explanations on the embodiments according to FIGS. 1 to 3 and, with respect to the connection of the sealing element 25 and the pressure piece 31, refer to the explanations on the embodiment according to FIG. 5.

Figure 7:
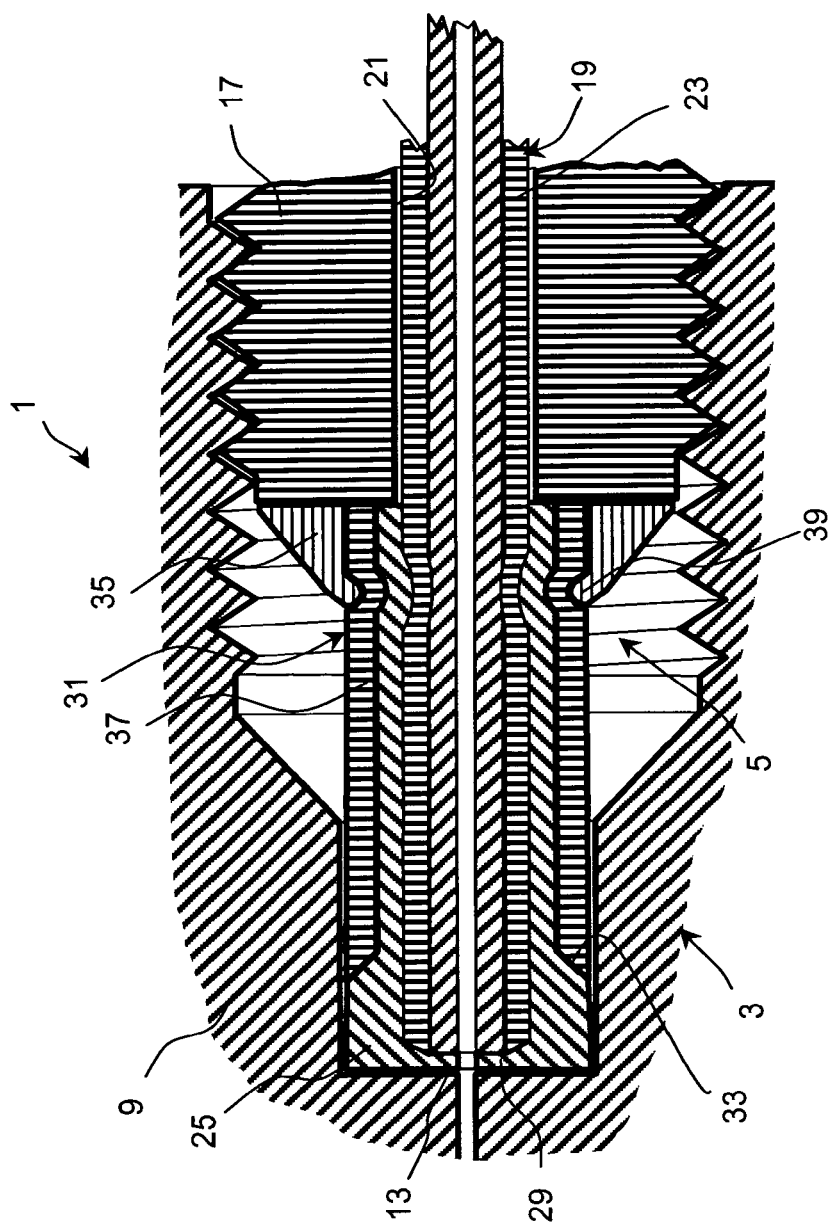

The embodiment according to FIG. 7 corresponds, in wide regions, to the embodiment according to FIG. 1, wherein, however, the front end surfaces of the pressure piece 31 or the base part 37 of the pressure piece 31 and the jacket layer 23 of the plug capillary tube 19 have a conical construction.

Through the conically outward-running construction of the end surface of the jacket layer 23, to generate axial pressure forces for the assembly of the plug unit 5 in the bushing unit 3, a compression of the material of the end wall 29 of the sealing element 25 is produced such that the material is forced outward with a radial component. Thus, there is a smaller risk that the through-flow opening or the bushing capillary tube opening 11 is narrowed or even closed by a radially inward-directed material flux due to the compression. In addition, through the conical shape of the end surface of the jacket layer 23, a smaller axial force is required to achieve material deformation or compression.

Figure 8:
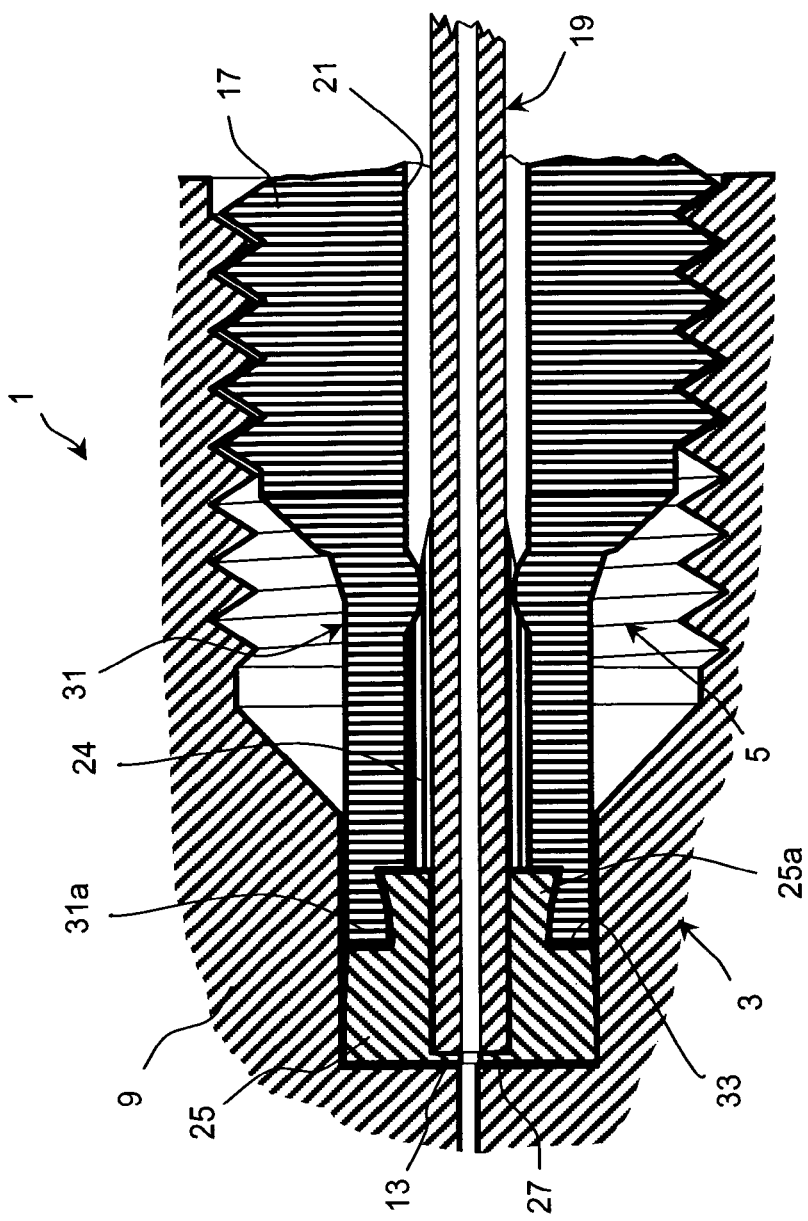

The same applies for the conically inward-directed end surface of the pressure piece 31 that interacts with a corresponding, conical shoulder 33 of the sealing element 25. Here, the axial tensile force that is required for separating the connection or for pulling out the plug unit 5 from the bushing unit 3 can be reduced. The embodiment of a connection system 1 according to FIG. 8 largely corresponds to the embodiment according to FIG. 6. In contrast to the embodiment according to FIG. 6, however, here a jacket element 24 is used that was applied before the assembly of the other components of the plug unit 5 on the inner wall of the plug capillary tube 19. Such a jacket element 24 can be produced, e.g., galvanically through electroforming or adhesion. The pressure piece 31 is pushed onto the plug capillary tube 19 with the jacket element 24 together with the sealing element up to the desired axial position and then the crimped connection is produced such that a positive-fit or positive-fit and non-positive-fit connection is formed between the pressure piece 31 and the jacket element 24. Obviously, the jacket element 24 could also be produced across a longer axial region on the plug capillary tube 19 than is shown in FIG. 8. If the end surface of the jacket element 24 does not reach up to the front end surface of the plug capillary tube 19 as shown in FIG. 8, then contact between the medium to be guided and the material of the jacket element 24 can be avoided. If this is not necessary, then obviously the jacket element can reach up to the end side of the plug capillary tube 19. In the same way, the jacket element 24 could also reach in the axially rearward direction into the axial region in which the plug capillary tube 19 is surrounded by the plug housing 17, for example, in order to avoid damage to the material of the plug capillary tube 19 in this region.

With all of the embodiments of a connection system 1 described above, a sealing effect is guaranteed directly on the front side of the plug capillary tube 19 or the sealing element 25 without an undesired dead volume being able to occur.

This also applies when the connection is detached and mounted again, possibly even when the same plug unit 5 is mounted in a different bushing unit 3 with a different axial length of the capillary tube receptacle opening 7 (within a permissible tolerance range). In addition, it is reliably avoided that the risk arises that the sealing element 25 remains in the capillary tube receptacle opening 7 when the plug unit 5 and bushing unit 3 are dismounted.

Obviously, individual features of embodiments that are explained above only in connection with the relevant figure could also be combined with other, not-shown embodiments, wherein these additional embodiments would also feature the named advantages.

As used herein, whether in the above description or the following claims, the terms "comprising," "including," "carrying," "having," "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The above described illustrative embodiments are intended to illustrate the principles of the invention, but not to limit the scope of the invention. Various other embodiments and modifications to these preferred embodiments may be made by those skilled in the art without departing from the scope of the present invention.

The invention claimed is:

1. A plug unit for connecting a capillary tube to a bushing unit of a high-pressure fluid handling system, the plug unit including:
   (a) a plug housing having an axial borehole;
   (b) a plug capillary tube projecting through the axial borehole of the plug housing;
   (c) an elongated annular sealing element through which a front end region of the plug capillary tube is received so that a front end surface of the plug capillary tube resides within a volume defined by the annular sealing element;
   (d) wherein the plug housing is adapted to detachably connect to the bushing unit;
   (e) a pressure piece through which a rear portion of the annular sealing element extends, the pressure piece having a front end spaced apart from a front end wall of the annular sealing element and having a rearward end surface that faces away from the front end wall of the annular sealing element, the pressure piece is in position to abut a shoulder of the annular sealing element;
   (f) wherein the pressure piece and the annular sealing element are both connected rigidly to the plug capillary tube so as to prevent relative movement between the pressure piece, the annular sealing element, and the plug capillary tube, and so that the front end region of the plug capillary tube, the annular sealing element, and the pressure piece are insertable simultaneously into a receptacle opening of the bushing unit with the front end region of the plug capillary tube projecting into a capillary tube receptacle opening of the bushing unit in alignment with a bushing capillary tube opening of the bushing unit; and
   (g) wherein when the front end region of the plug capillary tube, the annular sealing element, and the pressure piece are inserted into a fully inserted position in the receptacle opening of the bushing unit and the plug housing is placed in the connected position, the plug housing applies an axial force to the pressure piece, the annular sealing element, and the plug capillary tube so as to press at least the front end wall of the annular sealing element against a floor wall of the capillary tube receptacle opening of the bushing unit.

2. The plug unit of claim 1 wherein the front end region of the plug capillary tube has a hollow cylindrical construction with a constant cross section.

3. The plug unit of claim 1 or 2 wherein the annular sealing element includes a front end region which extends beyond a front end of the pressure piece and wherein an outer diameter of the annular sealing element front region corresponds to an outer diameter of the front end of the pressure piece.

4. The plug unit of claim 1 wherein an inner diameter of the annular sealing element corresponds to an outer diameter of the plug capillary tube.

5. The plug unit of claim 4 wherein the annular sealing element is formed from an elastic material so that the annular sealing element surrounds the plug capillary tube with a biasing tension when mounted on the front region of the plug capillary tube.

6. The plug unit of claim 1 wherein the rigid connection between the pressure piece, annular sealing element, and plug capillary tube is generated by a friction fit or by a friction fit and positive fit.

7. The plug unit of claim 6 wherein the pressure piece is connected through a crimped connection to the plug capillary tube or to the annular sealing element and the plug capillary tube.

8. The plug unit of claim 7 wherein the pressure piece has a two-part construction including a hollow cylindrical base part and an annular attachment part, and wherein the annular attachment part surrounds the base part and is crimped onto the base part so that the base part is also connected to the sealing element and the plug capillary tube, and wherein the annular attachment part has a triangular shape in longitudinal section and is crimped onto the base part with a radially inward crimp at an acute-angled section of the triangular shape.

9. The plug unit of claim 7 wherein the crimped connection is created at an axial position of the plug capillary tube at which the sealing element is surrounded by the pressure piece.

10. The plug unit of claim 1 wherein the plug capillary tube has at least one outer jacket layer at least in an axial sub-region that is encompassed by the pressure piece and wherein a crimped connection between the pressure piece and the plug capillary tube is formed in the axial sub-region.

11. A connection system for connecting a capillary tube in a high pressure fluid handling system, the connection system including:
   (a) a bushing unit having a receptacle opening in which is defined a capillary tube receptacle opening, the capillary tube receptacle opening including a floor wall and a bushing capillary tube opening located in the floor wall;
   (b) a plug unit including:
     (i) a plug housing having an axial borehole,
     (ii) a plug capillary tube projecting through the axial borehole of the plug housing,
     (iii) an elongated annular sealing element through which a front end region of the plug capillary tube is received so that a front end surface of the plug capillary tube resides within a volume defined by the annular sealing element, the annular sealing element having an outer diameter that corresponds, at least in a front axial sub-region of the annular sealing element, to an inner diameter of the capillary tube receptacle opening of the bushing unit, (iv) wherein the plug housing is adapted to detachably connect to the bushing unit, and (v) a pressure piece through which a rear portion of the annular sealing element extends, the pressure piece having a front end spaced apart from a front end wall of the annular sealing element and having a rearward end surface that faces away from the front end wall of the annular sealing element, the pressure piece is in position to abut a shoulder of the annular sealing element;

(c) wherein the pressure piece and the annular sealing element are both connected rigidly to the plug capillary tube so as to prevent relative movement between the pressure piece, the annular sealing element, and the plug capillary tube, and so that the front end region of the plug capillary tube, the annular sealing element, and the pressure piece are insertable simultaneously into the receptacle opening of the bushing unit with the front end region of the plug capillary tube projecting into the capillary tube receptacle opening in alignment with the bushing capillary tube opening; and (d) wherein when the front end region of the plug capillary tube, the annular sealing element, and the pressure piece are inserted into a fully inserted position in the receptacle opening and the plug housing is placed in the connected position, the plug housing applies an axial force to the pressure piece, the annular sealing element, and the plug capillary tube so as to press at least the front end wall of the annular sealing element against the floor wall of the capillary tube receptacle opening.

12. The connection system of claim 11 wherein the receptacle opening has a larger inner diameter than the capillary tube receptacle opening and the bushing unit includes a transition portion between the receptacle opening and the capillary tube receptacle opening.

13. The connection system of claim 11 wherein when the front end region of the plug capillary tube, the annular sealing element, and the pressure piece are inserted into the fully inserted position in the receptacle opening, the front end of the pressure piece reaches at least up to the capillary tube receptacle opening or extends into the capillary tube receptacle opening.

14. The connection system of claim 11 wherein the annular sealing element includes a front end region which extends beyond a front end of the pressure piece and wherein an outer diameter of the sealing element front region corresponds to an outer diameter of the front end of the pressure piece.

15. The connection system of claim 11 wherein an inner diameter of the annular sealing element corresponds to an outer diameter of the plug capillary tube.

16. The connection system of claim 15 wherein the annular sealing element is formed from an elastic material so that the annular sealing element surrounds the plug capillary tube with a biasing tension when mounted on the front region of the plug capillary tube.

17. The connection system of claim 11 wherein the rigid connection between the pressure piece, annular sealing element, and plug capillary tube is generated by a friction fit or by a friction fit and positive fit.

18. The connection system of claim 17 wherein the pressure piece is connected through a crimped connection to the plug capillary tube or to the annular sealing element and the plug capillary tube.

19. The connection system of claim 11 wherein the plug capillary tube has at least one outer jacket layer at least in an axial sub-region that is encompassed by the pressure piece and wherein a crimped connection between the pressure piece and the plug capillary tube is formed in the axial sub-region.

* * * * *